US00PP19985P2

(12) United States Plant Patent
Hooijman

(10) Patent No.: US PP19,985 P2
(45) Date of Patent: May 12, 2009

(54) ROSE PLANT NAMED 'ESM CANTATA'

(50) Latin Name: *Rosa hybrida*
Varietal Denomination: ESM Cantata

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 12/080,155

(22) Filed: Mar. 31, 2008

(51) Int. Cl.
*A01H 5/00* (2006.01)

(52) U.S. Cl. ..... Plt./134

(58) Field of Classification Search ..... Plt./134
See application file for complete search history.

*Primary Examiner*—Annette H Para
(74) *Attorney, Agent, or Firm*—C. A. Whealy

(57) ABSTRACT

A new and distinct cultivar of Rose plant named 'Esm Cantata', characterized by its long and upright flowering stems; durable foliage; yellow-colored flowers tinged with green and red; and excellent. postproduction longevity.

1 Drawing Sheet

Botanical designation: *Rosa hybrida.*

Cultivar denomination: 'ESM CANTATA'.

BACKGROUND OF THE INVENTION

The present Invention relates to a new and distinct cultivar of Rose plant, botanically known as *Rosa hybrida,* commercially used as a cut flower Rose, and hereinafter referred to by the name 'Esm Cantata'.

The new Rose is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new cultivar originated from a cross-pollination made by the Inventor in February, 2000 of a proprietary Rose selection identified as code number 93, not patented, as the female, or seed, parent with a proprietary Rose selection identified as code number 95, not patented, as the male, or pollen, parent. The cultivar Esm Cantata was discovered and selected by the Inventor as a single flowering plant within the progeny of the stated cross-pollination in a controlled environment in El Quinche, Pichincha, Ecuador in March, 2001.

Asexual reproduction of the new Rose by cuttings at El Quinche, Pichincha, Ecuador since April, 2001, has shown that the unique features of this new Rose are stable and reproduced true to type in successive generations of asexual reproduction.

SUMMARY OF THE INVENTION

The following traits have been repeatedly observed and are determined to be the unique characteristics of 'Esm Cantata'. These characteristics in combination distinguish 'Esm Cantata' as a new and distinct cultivar:

1. Long and upright flowering stems.
2. Durable foliage.
3. Yellow-colored flowers tinged with green and red.
4. Excellent postproduction longevity.

Plants of the new Rose differ from plants of the female parent selection in the following characteristics:

1. Plants of the new Rose are taller than plants of the female parent selection.
2. Plants of the new Rose have larger flowers than plants of female parent selection.
3. Plants of the new Rose and the female parent selection differ in flower color as plants of the female parent selection have solid yellow-colored flowers.

Plants of the new Rose differ from plants of the male parent selection in the following characteristics:

1. Plants of the new Rose have thorns whereas plants of the male parent selection do not have thorns.
2. Plants of the new Rose have larger flowers than plants of male parent selection.
3. Plants of the new Rose and the male parent selection differ in flower color as plants of the male parent selection have white and red purple bi-colored flowers.

Plants of the new Rose can be compared to plants of the Rose cultivar Golden Gate, not patented. In side-by-side comparisons conducted in El Quinche, Pichincha, Ecuador, plants of the new Rose differed from plants of the cultivar Golden Gate in the following characteristics:

1. Plants of the new Rose were shorter and narrower than plants of the cultivar Golden Gate.
2. Plants of the new Rose had smaller leaves than plants of the cultivar Golden Gate.
3. Plants of the new Rose had larger flower buds than plants of the cultivar Golden Gate.
4. Plants of the new Rose had larger flowers than plants of the cultivar Golden Gate.
5. Plants of the new Rose and the cultivar Golden Gate differed in flower color as plants of the cultivar Golden Gate had golden yellow-colored flowers.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph at the left of the sheet comprises a side perspective view of a typical flowering stem of 'Esm Cantata'.

The photograph at the top left of the sheet is a close-up view of a typical flower of 'Esm Cantata'.

The photographs at the bottom right of the sheet are close-up views of the upper and lower surfaces of typical leaves of 'Esm Cantata'.

DETAILED BOTANICAL DESCRIPTION

The new Rose has not been observed under all possible environmental conditions. The phenotype may vary somewhat with variations in environment such as temperature and light intensity, without, however, any variance in genotype. The aforementioned photographs, following observations and measurements describe plants grown in El Quinche, Pichincha, Ecuador, in a polyethylene-covered greenhouse and under commercial production practices. Plants were pinched about 13.5 weeks after planting. Plants were about 2.5 years old when the photographs and description were taken. During the production of the plants, day temperatures ranged from about 16° C. to 30° C., night temperatures ranged from about 12° C. to 16° C. and light levels ranged from about 800 to 1,200 foot-candles. In the following description, color references are made to The Royal Horticultural Society Colour Chart, 2001 Edition, except where general terms of ordinary dictionary significance are used.

Botanical classification: *Rosa hybrida* cultivar Esm Cantata

Parentage:

*Female, or seed, parent.*—Proprietary seedling selection of *Rosa hybrida* identified as code number 93, not patented.

*Male, or pollen, parent.*—Proprietary seedling selection of *Rosa hybrida* identified as code number 95, not patented.

Propagation:

*Type.*—By cuttings.

*Time to initiate roots.*—About seven to ten days at 26° C. to 30° C.

*Time to produce a rooted young plant.*—About four to five weeks at 22° C. to 26° C.

*Root description.*—Fibrous, thick; close to N199B in color.

*Rooting habit.*—Freely branching; moderately dense.

Plant description:

*Plant form.*—Upright plant habit; long and upright flowering stems.

*Growth habit.*—Vigorous; freely basal branching habit; dense and bushy growth habit; about 12 to 13 flowering stems develop per year.

*Plant height.*—About 90 cm to 100 cm.

*Plant width (spread).*—About 50 cm.

*Lateral branches (peduncles).*—Length: About 80 cm. Diameter: About 7 mm. Internode length: About 4.5 cm. Strength: Strong. Texture: Slightly pubescent. Color: Close to N199A. Thorns: Density: High. Shape: Triangular with sharp acuminate apices. Height: About 1 cm. Diameter, at base: About 0.9 mm. Color, immature: Close to 183C. Color, mature: Close to 185A.

Foliage description:

*Arrangement.*—Alternate; compound with typically five leaflets per leaf.

*Leaf length.*—About 15 cm.

*Leaf width.*—About 12 cm.

*Terminal leaflet length.*—About 7.4 cm.

*Terminal leaflet width.*—About 5.4 cm.

*Lateral leaflet length.*—About 6.5 cm.

*Lateral leaflet width.*—About 4.7 cm.

*Leaflet shaped.*—Ovate to oval.

*Leaflet apex.*—Acute.

*Leaflet base.*—Attenuate.

*Leaflet margin.*—Serrate.

*Leaflet texture, upper and lower surfaces.*—Smooth, glabrous.

*Leaflet venation pattern.*—Pinnate.

*Leaflet color.*—Developing leaflets, upper surface: Between 139A and 147A; occasionally towards the margins, tinted with N77A. Developing leaflets, lower surface: Close to 146B. Fully expanded leaflets, upper surface: Close to 139A; venation, close to 146A. Fully expanded leaflets, lower surface: Between 146B and 147B; venation, close to 146B.

*Petioles, leaves.*—Length: About 2.3 cm. Diameter: About 1.5 mm. Texture, upper and lower surfaces: Pubescent. Color, upper surface: Close to 181A. Color, lower surface: Close to 146A.

*Petioles, leaflets.*—Length: About 2.2 cm. Diameter: About 1.5 mm. Texture, upper and lower surfaces: Pubescent. Color, upper surface: Close to N199A; towards the margin, 181B. Color, lower surface: Close to 146A.

*Stipules.*—Quantity/arrangement/appearance: Two, adnate to the petiole, leafy. Length: About 3.3 cm. Width: About 3.5 mm. Shape: Roughly deltoid. Apex: Acuminate. Base: Truncate. Margin: Serrate, irregular. Texture, upper and lower surfaces: Smooth, glabrous. Venation pattern: Pinnate. Color, upper surface: Close to 137A. Color, lower surface: Close to 146A.

Flower description:

*Flower type and habit.*—Yellow-colored flowers tinged with green and red. Consistently symmetrical rosette flowers; one flower per terminal. Flowers persistent.

*Flowering season.*—Year-round under greenhouse conditions, optimal flowering from spring through autumn under garden conditions; flowering intermittent.

*Flower diameter.*—About 12.2 cm.

*Flower depth (height).*—About 5.5 cm.

*Flower longevity on plant.*—About 30 days.

*Flower longevity as a cut flower.*—About 15 days.

*Fragrance.*—Not detected.

*Flower buds.*—Shape: Ovoid. Length: About 5.3 cm. Diameter: About 3.7 cm. Color: Between 143A and 148A; towards the apex, close to 187B.

*Petals.*—Quantity: Numerous; about 31 per flower. Length: About 5.3 cm. Width: About 6.2 cm. Shape: Nearly round. Apex: Rounded, cuspidate. Base: Obtuse. Margin: Entire. Texture, upper and lower surfaces: Smooth, glabrous. Color: When opening, upper surface: Close to 9A. When opening, lower surface: Close to 8B; towards the apex, close to 45A. Fully opened, upper surface: Close to 9A; towards the margin, close to 46A to 46B. Older petals tinged with close to 144A. Fully opened, lower surface: Close to 12A; towards the center and apex, close to 46A to 46B. Older petals tinged with close to 144A.

*Sepals.*—Quantity per flower: Typically five. Length: About 5.4 cm. Width: About 1.2 cm. Shape: Roughly deltoid. Apex: Tapered. Base: Truncate. Margin: Entire; ciliate. Texture, upper and lower surfaces: Pubescent; rugose; leathery. Color: When opening, upper surface: Close to 146D; towards the apex, close to 199A. When opening, lower surface: Close to 146B; towards the margin, close to 178A. Fully opened, upper surface: Close to 146B; towards the apex, close to N 199A. Fully opened, lower surface: Close to 146A; towards the margin, close to 183C.

*Reproductive organs.*—Stamens: Quantity: About 190 per flower. Anther length: About 3 mm. Anther shape: Reniforn. Anther color: Close to 7A. Filament color: Close to 15D. Pollen amount: Scarce. Pollen color: Close to N163D. Pistils: Quantity: About 270 per flower. Pistil length: About 1.7 cm. Stigma shape: Broadly reniform. Stigma color: Close to 5C. Style length: About 1.1 cm. Style color: Close to 157D. Receptacle height: About 1.3 cm. Receptacle diameter: About 1.3 cm. Receptacle shape: Cup-shaped. Receptacle texture: Smooth, glabrous. Receptacle color: Close to 143C. Seeds/fruits: Seed and fruit development has not been observed on plants of the new Rose.

Pathogen/pest resistance: Plants of the new Rose have been observed to be resistant to *Botrytis*. Plants of the new Rose have not been observed to be resist to pests and other pathogens common to Roses.

Temperature tolerance: Plants of the new Rose have been observed to tolerate temperatures ranging from 0° C. to 35° C.

It is claimed:

1. A new and distinct Rose plant named 'Esm Cantata' as illustrated and described.

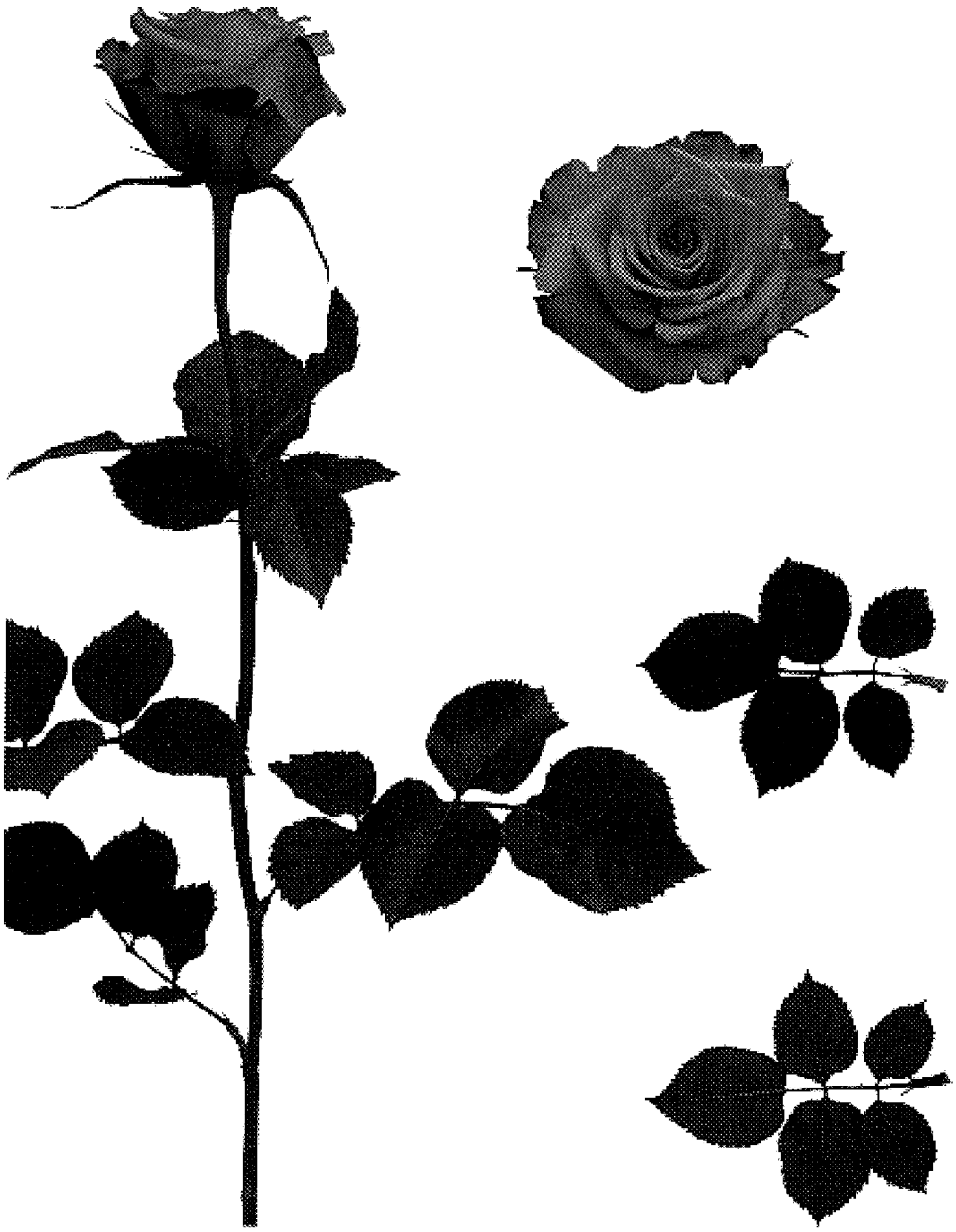

* * * * *